(12) United States Patent
Kang et al.

(10) Patent No.: US 6,740,671 B2
(45) Date of Patent: May 25, 2004

(54) FUNGICIDAL COMPOSITION CONTAINING N-(α-CYANO-2-THENYL)-4-ETHYL-2-(ETHYLAMINO)-5-THIAZOLECARBOXAMIDE

(75) Inventors: Kyung-Goo Kang, Taejon (KR); Seung-Hun Kang, Taejon (KR); Dal-Soo Kim, Taejon (KR); Hyun-Cheol Park, Taejon (KR); Sam-Jae Chun, Taejon (KR); Sang-Who Lee, Taejon (KR); Jin-Ho Cho, Taejon (KR); Kwang-Yun Cho, Taejon (KR); Ju-Hyun Yu, Taejon (KR); He-Kyoung Lim, Taejon (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

(21) Appl. No.: 10/275,653

(22) PCT Filed: May 9, 2001

(86) PCT No.: PCT/KR01/00754

§ 371 (c)(1),
(2), (4) Date: Nov. 8, 2002

(87) PCT Pub. No.: WO01/84930

PCT Pub. Date: Nov. 15, 2001

(65) Prior Publication Data

US 2003/0203949 A1 Oct. 30, 2003

(30) Foreign Application Priority Data

May 10, 2000 (KR) .......................... 2000-25096

(51) Int. Cl.$^7$ .................. A01N 43/78; A01N 43/36; A61K 31/425
(52) U.S. Cl. .................. 514/370; 504/138; 504/266
(58) Field of Search .................. 504/138, 266; 514/370

(56) References Cited

U.S. PATENT DOCUMENTS 5,411,955 A 5/1995 Strasser et al.
5,438,070 A 8/1995 Eicken et al.

*Primary Examiner*—Alton N. Pryor
(74) *Attorney, Agent, or Firm*—Birch, Stewart, Kolasch & Birch, LLP

(57) ABSTRACT

The present invention relates to a fungicidal composition which comprises N-(α-cycno-2-thenyl)-4-ethyl-2-(ethylamino)-5-thiazolecarboxamide (ethaboxam) and as an adjuvant polyoxyalkylene alkyl ether.

7 Claims, No Drawings

FUNGICIDAL COMPOSITION CONTAINING N-(α-CYANO-2-THENYL)-4-ETHYL-2-(ETHYLAMINO)-5-THIAZOLECARBOXAMIDE

This application is the national phase under 35 U.S.C. §371 of PCT International Application No. PCT/KR01/00754 which has an International filing date of May 9, 2001, which designated the United States of America.

TECHNICAL FIELD

The present invention relates to a novel fungicidal composition comprising a 2-aminothiazolecarboxamide derivative, N-(α-cyano-2-thenyl)-4-ethyl-2-(ethylamino)-5-thiazolecarboxamide (ISO proposed name: ethaboxam) of the formula:

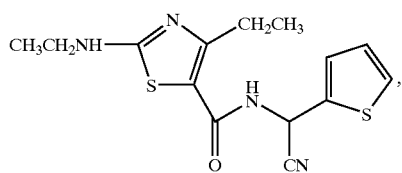

(I)

and as an adjuvant a suitable nonionic surfactant.

BACKGROUND ART

A compound of formula (I), ethaboxam, was already described as a fungicidal compound for crop protection in Korean Patent No. 124,552 (Korean patent application No. 94-19960). Further, ethaboxam-containing formulations, e.g. wettable powder (trade name: Guardian; marketed by Misung Ltd.) were known.

An adjuvant is a non-pesticidal compound for enhancing a total activity of a pesticide, differently from a co-formulant which controls physical properties of active ingredients to facilitate their handling. Presence of the adjuvant in a pesticidal formulation increases a total quantity of active ingredients which can be contacted with and/or penetrated into a target plant thereby to enhance the activity of pesticide and to remarkably reduce the quantity of active ingredients which needs to be applied. Currently, Environmental Protection Agency in the U.S.A. and Ministry of Agriculture, Fisheries and Food in the United Kingdom are recognizing the employment of the adjuvant as a major tool for obtaining desired activity of novel active ingredients.

An adjuvant is widely used in leading advanced countries such as the U.S.A. and European countries and conventionally, is manufactured and marketed as a separate package for use as a tank-mix formulation in spraying herbicides. Recently, its application is also extended to fungicides, insecticides, growth regulators and fertilizers. However, the adjuvant for use as the tank-mix formulation is manufactured as a separate package and thus, its production and transportation costs are unavoidably increased and particularly, strict experimental data are required for its registration. Therefore, its development takes a long time and requires enormous expenses.

Recently, several leading agrochemical manufacturers are likely to formulate an adjuvant in combination with active ingredients in one package thereby to facilitate mixing, transportation and particularly, registration of products. A formulation containing the adjuvant in combination with the active ingredients in one package is referred to as a premixed one-pack formulation, a contrary concept to a tank-mixed formulation. An example of the premixed one-pack formulations is a round-up formulation containing as the adjuvant tallow amine and as the herbicidal compound glyphosate in one package.

Conventionally, an adjuvant for fungicides is added to a spray liquid when applied and a product containing 75–95% of a mineral oil and 5–25% of a surfactant is widely used. This adjuvant increases the fungicidal activity by improving the retention of active ingredients to plants rather than by increasing foliar penetration of active ingredients. However, such mineral oil-containing product may cause injury to plants and environmental contamination due to its low biodegradability.

Recently, in order to increase the efficacy of high-activity penetrative fungicides, it was suggested that non-ionic surfactants such as sorbitan esters of fatty acids, polyoxyethylene alkyl ethers, polyoxyethylene sorbitan esters, polyoxyethylene alkyl phenol ethers, polyoxyethylene amides be incorporated into the fungicides (see U.S. Pat. No. 5,905,072). Examples of fungicides which can be employed are as follows: triazoles, e.g. tetraconazole, triadimefon, triadimenol, propiconazole, penconazole, hexaconazole, cyproconazole, flusilazole, etc.; imidazoles, e.g. prochloraz, imazalil, etc.; morpholines, e.g. fenpropimorph, tridemorph, etc.; dicarboxyimides, e.g. iprodione, vinclozolin, etc.; piperidines, e.g. fenprodipin, etc.; acyl alanines, e.g. metalaxyl, benalaxyl, etc. In particular, it was disclosed that polyoxyethylene alkyl ethers selectively enhance the efficacy of the penetrative fungicide, benzyl triazolyl cyclopentanes (see U.S. Pat. No. 5,393,770).

Accordingly, in order to enhance the fungicidal activity of ethaboxam and to reduce the quantity thereof which needs to be applied, screening of an environment friendly adjuvant and development of a novel fungicidal composition using the same may provide many advantages in both commercial and environmental aspects.

DISCLOSURE OF THE INVENTION

In order to develop a compound enhancing the efficacy of ethaboxam and reducing its quantity which needs to be applied, the present inventors incorporated various potential compounds including anionic and nonionic surfactants into ethaboxarnp. and conducted experiments for their efficacy enhancement activity. As a result, they found that nonionic surfactants of polyoxyalkylene alkyl ether class cause enhancement of activity. Thus, they prepared a one-pack formulation containing them, and found that such formulation remarkably enhances the fungicidal activity at a given level of ethaboxam. Further, they found that the formulation containing a particular polyoxyalkylene alkyl ether has equivalent or superior efficacy evenat a half or less level of ethaboxam, as compared with polyoxyalkylene alkyl ether-free ethaboxam formulation and thus, completed the present invention.

Thus, it is an object of the present invention to provide a fungicidal composition comprising ethaboxam and a non-pesticidal adjuvant which is more cost-effective and readily biodegradable than active ingredients.

A first aspect of the present invention provides a fungicidal composition which comprises N-(α-cyano-2-thenyl)-4ethyl-2-(ethylamino)-5-thiazolecarboxamide of the formula:

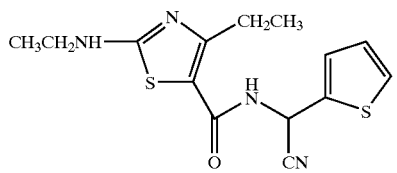

(I)

(hereinafter, referred to as ethaboxam) and a nonionic surfactant.

A further aspect of the present invention provides a method for enhancing the activity of ethaboxam, which comprises adding a nonionic surfactant to ethaboxam formulation.

A still further aspect of the present invention provides a method for controlling undesired phytopathogens which comprises applying a formulation prepared from the composition of the present invention to target plants.

The nonionic surfactant which can be employed in the present invention is classified into polyoxyalkylene alkyl ether having polyoxyalkylene as the hydrophilic moiety and aliphatic alcohol as the lipophilic moiety. Preferred polyoxyalkylene alkyl ether is derived from saturated or unsaturated alcohol having the alkyl chain of 12 to 18 carbon atoms or mixtures thereof More preferred polyoxyalkylene alkyl ether is derived from lauryl alcohol having 12 carbon atoms, cetyl alcohol having 16 carbon atoms, stearyl alcohol being saturated and having 18 carbon atoms or oleyl alcohol being unsaturated and having 18 carbon atoms. In the present invention, polyoxyethylene is representative polyoxyalkylene, but polyoxyethylene-polyoxypropylene copolymer wherein ethylene oxide and propylene oxide is copolymerized is also included. For example, polyoxyethylene has an average of 3 to 50, more preferably, 7 to 20, most preferably, 10 to 14 ethylene oxide units per molecule, depending upon the number of carbon atoms in the alkyl chain derived from aliphatic alcohol. In the present invention, particularly preferred is polyoxyethylene lauryl ether, polyoxyethylene cetyl ether, polyoxyethylene stearyl ether or polyoxyethylene oleyl ether, each of which has an average of 7 to 20 ethylene oxide units per molecule. Polyoxyalkylene alkyl ether employed in the present invention may be obtained by copolymerization of ethylene oxide and natural or synthetic aliphatic alcohol having 12 to 18 carbon atoms and the purity of 50 to 98%.

The fungicidal composition of the present invention contains 1 to 80 wt %, preferably, 5 to 50 wt % of ethaboxam, 10 to 50 wt % of adjuvant, 10 to 89 wt/% of solid or liquid carrier or additive and 0 to 20 wt %, preferably, 0.1 to 10 wt % of surfactants. In case where the composition contains less than 1 wt % of ethaboxam, it is difficult to control the dilution fold. By contrast, in case where the composition contains more than 80 wt % of ethaboxam, it is difficult to maintain physical properties of formulations.

In the composition of the present invention, the presence of polyoxyalkylene alkyl ether reduces the quantity of ethaboxam which needs to be applied to obtain a given level of activity to a significant extent. Practically, a concentration of ethaboxam in a spray for controlling downy mildew is approximately 250 mg/l. But, in case of containing 100 to 2000 mg/l of a particular polyoxyalkylene alkyl ether in a premixed oiie-pack or tank-mixed formulation, even at a half or less concentration of ethaboxam, the efficacy is equivalent or superior to that of the polyoxyalkylene alkyl ether-free formulation.

In the composition for one-pack formulation, an adjuvant is comprised at 10 to 50% by weight. Enhancement of activity can be obtained not only in a one-pack formulation but also in a tank-mixed formulation. But, the concentration of the adjuvant is not fixed in the tank-mixed formulation, differently in the one-pack formulation. It is suggested that enhancement of the activity by addition of adjuvant results from the increase of the permeability into plants by improvement of foliar penetration. This can be inferred from the differences in permeability according to the concentration of adjuvant.

In the present invention, a weight ratio of ethaboxam to adjuvant ranges from about 1:0.5 to about 1:10, preferably, from about 1:1 to about 1:5.

The fungicidal composition in accordance with the present invention is effective for preventing or curing plant diseases caused by phytopathogens as follows: gerbera phytophthora root rot (*Phytophthora cryptogea*), potato late blight (*Phytophthora infestans*), hot pepper phytophthora blight (*Phytopthora capsici*), tomato late blight (*Phytophtliora infestans*), tobacco black shank (*Phytophthora nicotianae* var. nicotianae), sesame rot (*Phytophthora nicotianae* var. *parasitica*), apple phytophthora fruit rot (*Phytophthora cactorum*), *Cucumis melo L.* var. *makuzwa* MAKINO downy mildew (*Pseudoperonospora cubensis*), melon downy mildew (*Pseudoperonospora cubensis*), cucumber downy mildew (*Pseudoperonospora cubensis*), cabbage downy mildew (*Peronospora parasitica*), lettuce downy mildew (*Bremia lactucae*), rose downy mildew (*Peronospora sparsa*), grape downy mildew (*Plasmopara viticola*), hop downy mildew (*Pseudoperospora humuli*) and turf grass Pythium blight (Phythium spp.)

If desired, the fungicidal composition of the present invention contains carriers, surfactants or co-formulants conveniently used in the pesticide formulation area. For example, the composition is processed to unreformed forms, for example, to formulations such as wettable powder prepared by homogeneously mixing active ingredient with extender (e.g. solvent, solid carriers and if appropriate, surfactants) and/or grinding the mixture, dispersible concentrate, emulsifiable concentrate, water dispersible granule, suspension concentrate, oil flowable, etc. and applied by spraying onto foliage and stems of plants. Application frequency and application rate are varied depending on biological properties of pathogens and weather environment. Suitable carrier and additive may be solid or liquid which is generally used in the pesticide formulation, for example, natural or synthetic inorganic materials, solvent, dispersing agents, wetting agents, diluents and the like. Employable solvent is polar solvent such as N-methyl-2-pyrrolidone, dimethyl sulfoxide or dimethyl fornamide. Auxiliary solvent is long-chain alcohol such as N-octyl-2-pyrrolidone, substituted naphthalene, xylene, substituted benzene, decyl alcohol, dodecyl alcohol, etc. and long-chain ester compounds. Employable solid carrier is micronized natural mineral such as talc, kaolin, calcium carbonate, diatomite or pyrophyllite. Moreover, to improve physical properties, particularly wettability, of formulation, a water-soluble ionic compound such as anhydrous sodium sulfate or hydrophilic porous synthetic compound may be employed.

An adjuvant may be adsorbed with an adsorbent such as high-dispersible synthetic silica or high-dispersible adsorbing polymer, etc. (e.g. white carbon, synthetic calcium silicate) within the range of having no harmful effects on storage stability, particularly, at a weight ratio of the adjuvant to the adsorbent ranging from 2:1 to 1:1. Surfactants having various properties may be used depending upon the type of ethaboxam formulations, but suitable is nonionic or anionic surfactant having good wettability and dispersibility. As used herein, surfactants include mixtures thereof A wetting agent employable in the present invention includes anionic wetting agent such as sodium lauryl sulfate, polyoxyalkylene alkyl phenyl ether sulfonate, dialkyl sulfosuccinate, dialkyl naphthalene sulfonate, polyoxyalkylene alkyl ether sulfate, etc., nonionic wetting agent such as acetylene classes and urea complex of non-ionic surfactant. More preferred is sodium lauryl sulfate, polyoxyalkylene alkyl phenyl ether sulfonate, polyoxyalkylene alkyl ether sulfate or urea complex of nonionic surfactant, etc.

In powder formulations, dispersing agent includes anionic dispersing agent such as lignin sulfonate, naphthalene sulfonate, lauryl sulfate, lauryl sulfonate, polyoxyalkylene alkyl aryl ether sulfate, polyoxyalkylene alkyl ether sulfate, etc. and nonionic dispersing agent such as polyoxyalkylene alkyl aryl ether, polyoxyalkylene alkyl ether, etc. However, in case of using polyoxyethylene cetyl ether or polyoxyethylene stearyl ether with an average of 10 or more ethylene oxide units per molecule as adjuvant, additional dispersing agent may not be comprised because the adjuvant may also function as the dispersing agent. In liquid formulations, dispersing agent such as nonionic dispersing agent with a high dispersibility, for example, polyoxyalkylene alkyl aryl ether, preferably, polyoxyalkylene tristyryl phenol ether or polyoxyalkylene alkyl ether, etc. may be used. In many cases, such dispersing agent is also useful as wetting agent. Wetting and dispersing agents are not limited to those as mentioned above, and may be selected among suitable nonionic or anionic surfactants.

The fungicidal composition of the present invention may be manufactured into premixed one-pack formulations by mixing ethaboxam and adjuvant with carrier or surfactant or tank-mixed formulations. In this case, the concentrations of ethaboxam and adjuvant are adjusted to about 30 to about 300 mg/l and about 100 to 2000 mg/l, respectively.

The composition according to the present invention may further comprise one or more additional agents for preventing or curing plant diseases, which include, but are not limited to, azoxystrobin, copper oxychloride, cymoxanil, dimethomorph, famoxadone, fluazinam, metalaxyl, oxadixyl, chlorothalonil, dithianon, folfet, mancozeb, propineb, etc.

In the present invention, wettable powder may be prepared by the following procedure: ethaboxam is mixed with co-formulants other than adjuvant and absorbent and the mixture is ground using a suitable mill. Adjuvant is previously adsorbed to adsorbent such as white carbon, etc. and ground by Warning blender. Then, the two ground parts are homogeneously mixed to obtain the fungicidal composition. On the other hand, dispersible concentrate may be prepared by the following procedure: active ingredient, adjuvant and other co-formulants are dissolved using a suitable mixer to obtain the homogenous combination.

BEST MODE FOR CARRYING OUT THE INVENTION

Hereinafter, the present invention will be explained in more detail with reference to the following examples. However, these examples are merely illustrative of, and are not intended to, nor should be intended to, limit the present invention.

Formulations having the compositions as set forth in the following tables were prepared. Unless specifically indicated, n represents an average of ethylene oxide units per molecule. In the tables, KONION and Brij represent products by Korea Polyol (Korea) and UniQema (UK), respectively and Koremul and HY by Han Nong Chemicals (Korea).

EXAMPLES 1 to 5

Preparation of Wettable Powder

Polyoxyethylene alkyl ether was previously adsorbed to white carbon and ground by Warning blender. Ethaboxam was homogeneously mixed with other co-formulants using a vinyl bag and then, the mixture was ground in a mill. Then, the two ground parts were homogeneously mixed to obtain the wettable powder (Table 1).

TABLE 1

| Example | 1 | 2 | 3 | 4 | 5 |
|---|---|---|---|---|---|
| Ethaboxam | 12.5 | 12.5 | 12.5 | 12.5 | 12.5 |
| Polyoxyethylene(n = 10) lauryl ether (KONION LA-10) | 40 | — | — | — | — |
| Polyoxyethylene(n = 20) lauryl ether (KONION LA-20) | — | 40 | — | — | — |
| Polyoxyethylene(n = 10) cetyl ether (Brij 56) | — | — | 40 | — | — |
| Polyoxyethylene(n = 12) cetyl ether (Koremul CE-12) | — | — | — | 40 | — |
| Polyoxyethylene(n = 20) cetyl ether (Brij 58) | — | — | — | — | 40 |
| Anhydrous sodium sulfate | 15.5 | 15.5 | 15.5 | 15.5 | 15.5 |
| Sodium lauryl sulfate | 2 | 2 | 2 | 2 | 2 |
| Sodium lignin sulfonate | 3 | 3 | 3 | 3 | 3 |
| White carbon(Zeosil 39) | 27.0 | 27.0 | 27.0 | 27.0 | 27.0 |

(unit: weight %)

EXAMPLES 6 to 10

Preparation of Wettable Powder

Wettable powder having the composition as set forth in Table 2 was prepared according to the substantially same procedure as Examples 1 to 5.

TABLE 2

| Example | 6 | 7 | 8 | 9 | 10 |
|---|---|---|---|---|---|
| Ethaboxam | 12.5 | 12.5 | 12.5 | 12.5 | 12.5 |
| Polyoxyethylene(n = 15) oleyl ether (KONION OA-15) | 40 | — | — | — | — |
| Polyoxyethylene(n = 20) oleyl ether (Koremul OE-20) | — | 40 | — | — | — |
| Polyoxyethylene(n = 10) stearyl ether (Brij 76) | — | — | 40 | — | — |
| Polyoxyethylene(n = 14) stearyl ether (Koremul SE-14) | — | — | — | 40 | — |
| Polyoxyethylene(n = 20) stearyl ether (Brij 78) | — | — | — | — | 40 |
| Anhydrous sodium sulfate | 15.5 | 15.5 | 15.5 | 15.5 | 15.5 |
| Sodium lauryl sulfate | 2 | 2 | 2 | 2 | 2 |
| Sodium lignin sulfonate | 3 | 3 | 3 | 3 | 3 |
| White carbon(Zeosil 39) | 27.0 | 27.0 | 27.0 | 27.0 | 27.0 |

(unit: weight %)

EXAMPLES 11 to 13

Preparation of Wettable Powder

Wettable powder having the composition as set forth in Table 3 was prepared according to the substantially same procedure as Examples 1 to 5.

TABLE 3

| Example | 11 | 12 | 13 |
|---|---|---|---|
| Ethaboxam | 12.5 | 12.5 | 12.5 |
| Polyoxyethylene(n = 12) cetyl ether(Koremul CE-12) | 12.5 | 25.0 | 37.5 |
| Anhydrous sodium sulfate | 15.5 | 15.5 | 15.5 |
| Sodium lauryl sulfate | 2 | 2 | 2 |
| Sodium lignin sulfonate | 3 | 3 | 3 |
| White carbon(Zeosil 39) | 27 | 27 | 27 |
| Kaolin | 27.5 | 15 | 2.5 |

(unit: weight %)

EXAMPLES 14 to 16

Preparation of Dispersible Concentrate

Ethaboxam was previously dissolved in N-methyl-2-pyrrolidone to which were added other co-formulants and adjuvant and dissolved to obtain the dispersible concentrate (Table 4).

TABLE 4

| Example | 14 | 15 | 16 |
|---|---|---|---|
| Ethaboxam | 12.5 | 12.5 | 12.5 |
| Polyoxyethylene(n = 7) lauryl ether(KONION LA-7) | 25 | — | — |
| Polyoxyethylene(n = 10) lauryl ether(KONION LA-10) | — | 25 | — |
| Polyoxyethylene(n = 20) lauryl ether(KONION LA-20) | — | — | 25 |
| Polyoxyethylene tristyryl phenyl ether(HY-310F) | 5 | 5 | 5 |
| N-methyl-2-pyrrolidone | 57.5 | 57.5 | 57.5 |

(unit: weight %)

EXAMPLES 17 to 20

Preparation of Dispersible Concentrate

Dispersible concentrate having the composition as set forth in Table 5 was prepared according to the substantially same procedure as Examples 14 to 16.

TABLE 5

| Example | 17 | 18 | 19 | 20 |
|---|---|---|---|---|
| Ethaboxam | 12.5 | 12.5 | 12.5 | 12.5 |
| Polyoxyethylene(n = 7) cetyl ether(Koremul CE-7) | 25 | — | — | — |
| Polyoxyethylene(n = 10) cetyl ether(Brij 56) | — | 25 | — | — |
| Polyoxyethylene(n = 15) cetyl ether (Koremul CE-12) | — | — | 25 | — |
| Polyoxyethylene(n = 20) cetyl ether(Brij 58) | — | — | — | 25 |
| Polyoxyethylene tristyryl phenyl ether (HY-310F) | 5 | 5 | 5 | 5 |
| N-methyl-2-pyrrolidone | 57.5 | 57.5 | 57.5 | 57.5 |

(unit: weight %)

EXAMPLES 21 to 24

Preparation of Dispersible Concentrate

Dispersible concentrate having the composition as set for in Table 6 was prepared according to the substantially same procedure as Examples 14 to 16.

TABLE 6

| Example | 21 | 22 | 23 | 24 |
|---|---|---|---|---|
| Ethaboxam | 12.5 | 12.5 | 12.5 | 12.5 |
| Polyoxyethylene(n = 7) oleyl ether(Koremul OE-7) | 25 | — | — | — |
| Polyoxyethylene(n = 10) oleyl ether (Koremul OE-10) | — | 25 | — | — |
| Polyoxyethylene(n = 15) oleyl ether (KONION OA-15) | — | — | 25 | — |
| Polyoxyethylene(n = 20) oleyl ether (Koremul OE-20) | — | — | — | 25 |
| Polyoxyethylene tristyryl phenyl ether (HY-310F) | 5 | 5 | 5 | 5 |
| N-methyl-2-pyrrolidone | 57.5 | 57.5 | 57.5 | 57.5 |

(unit: weight %)

EXAMPLES 25 to 28

Preparation of Dispersible Concentrate

Dispersible concentrate having the composition as set forth in Table 7 was prepared according to the substantially same procedure as Examples 14 to 16.

TABLE 7

| Example | 25 | 26 | 27 | 28 |
|---|---|---|---|---|
| Ethaboxam | 12.5 | 12.5 | 12.5 | 12.5 |
| Polyoxyethylene(n = 7) stearyl ether (Koremul SE-7) | 25 | — | — | — |
| Polyoxyethylene(n = 10) stearyl ether(Brij 76) | — | 25 | — | — |
| Polyoxyethylene(n = 14) stearyl ether (Koremul SE-14) | — | — | 25 | — |
| Polyoxyethylene(n = 20) stearyl ether(Brij 78) | — | — | — | 25 |
| Polyoxyethylene tristyryl phenyl ether(HY-310F) | 5 | 5 | 5 | 5 |
| N-methyl-2-pyrrolidone | 57.5 | 57.5 | 57.5 | 57.5 |

(unit: weight %)

EXAMPLES 29 to 31

Preparation of Dispersible Concentrate

Dispersible concentrate having the composition as set forth in Table 8 was prepared according to the substantially same procedure as Examples 14 to 16.

TABLE 8

| Example | 29 | 30 | 31 |
|---|---|---|---|
| Ethaboxam | 8.5 | 8.5 | 8.5 |
| Polyoxyethylene(n = 12) cetyl ether (Koremul CE-12) | 17.0 | 25.5 | 34.0 |
| Polyoxyethylene tristyryl phenyl ether(HY-310F) | 10 | 10 | 10 |
| N-methyl-2-pyrrolidone | 64.5 | 56.0 | 47.5 |

(unit: weight %)

EXAMPLES 32 to 36

Preparation of Wettable Powder

Wettable powder having the composition as set forth in Table 9 was prepared according to the substantially same procedure as Examples 1 to 5.

TABLE 9

| Example | 32 | 33 | 34 | 35 | 36 |
|---|---|---|---|---|---|
| Ethaboxam | 7 | 7 | 7 | 7 | 7 |
| Azoxystrobin[1] | 5 | — | — | — | — |
| Copper oxychloride[2] | — | 30 | — | — | — |
| Cymoxanil[3] | — | — | 6 | — | — |
| Dimethomorph[4] | — | — | — | 15 | — |
| Famoxadone[5] | — | — | — | — | 9 |
| Polyoxyethylene(n = 12) cetyl ether (Koremul CE-12) | 40 | 30 | 40 | 40 | 40 |
| Sodium lauryl sulfate | 2 | 2 | 2 | 2 | 2 |
| White carbon(Zeosil 39) | 26.7 | 20 | 26.7 | 26.7 | 26.7 |
| Anhydrous sodium sulfate | 19.3 | 11 | 18.3 | 9.3 | 15.3 |

(unit: weight %)
[1]Methyl-(E)-2-{2-[6-(2-cyanophenoxy)pyrimidin-4-yloxy]phenyl}-3-methoxy acrylate
[2]Dicopper chloride trihydroxide
[3]1-(2-Cyano-2-methoxyiminoacetyl)-3-ethylurea
[4](E,Z)-4-[3-(4-chlorophenyl)-3-(3,4-dimethoxyphenyl)acryloyl]morpholine
[5]3-Anilino-5-methyl-5-(4-phenoxyphenyl)-1,3-oxazolidin-2,5-dione EXAMPLES 37 to 39

Preparation of Wettable Powder

Wettable powder having the composition as set forth in Table 10 was prepared according to the substantially same procedure as Examples 1 to 5.

TABLE 10

| | Example | | |
|---|---|---|---|
| | 37 | 38 | 39 |
| Ethaboxam | 7 | 7 | 7 |
| Fluazinam[1] | 12.5 | — | — |
| Metalaxyl[2] | — | 12.5 | — |
| Oxadixyl[3] | — | — | 16 |
| Polyoxyethylene(n = 12) cetyl ether(Koremul CE-12) | 40 | 40 | 40 |
| Sodium lauryl sulfate | 2 | 2 | 2 |
| White carbon(Zeosil 39) | 26.7 | 26.7 | 26.7 |
| Anhydrous sodium sulfate | 11.8 | 11.8 | 8.3 |

(unit: weight %)
[1]3-Chloro-N-[3-chloro-5-trifluoromethyl-2-pyridyl]-α,α,α-trifluoro-2,6-dinitro-p-toluidine
[2]Methyl N-(methoxyacetyl)-N-(2,6-xylyl)-DL-alaninate
[3]2-Methoxy-N-(2-oxo-1,3-oxazolidin-3-yl)aceto-2',6'-xylidide EXAMPLES 40 to 44

Preparation of Wettable Powder

Wettable powder having the composition as set forth in Table 11 was prepared according to the substantially same procedure as Examples 1 to 5.

TABLE 11

| | Example | | | | |
|---|---|---|---|---|---|
| | 40 | 41 | 42 | 43 | 44 |
| Ethaboxam | 3.5 | 3.5 | 3.5 | 3.5 | 3.5 |
| Chlorothalonil[1] | 60 | — | — | — | — |
| Dithianone[2] | — | 30 | — | — | — |
| Folfet[3] | — | — | 20 | — | — |
| Mancozeb[4] | — | — | — | 50 | — |
| Propineb[5] | — | — | — | — | 50 |
| Polyoxyethylene(n = 12) cetyl ether(Koremul CE-12) | 15 | 30 | 30 | 15 | 15 |
| Sodium lauryl sulfate | 2 | 2 | 2 | 2 | 2 |
| White carbon(Zeosil 39) | 10 | 20 | 10 | 10 | 10 |
| Anhydrous sodium sulfate | 9.5 | 14.5 | 24.5 | 19.5 | 19.5 |

(unit: weight %)
[1]Tetrachloroisophthalonitrile
[2]5,10-Dihydro-5,10-dioxonaphtho[2,3-b]-1,4-dithiin-2,3-dicarbonitrile
[3]N-(trichloromethylthio)phthalimide
[4](Polymerized) Complex of zinc salt and manganese ethylene bis (dithiocarbamate)
[5]Polymerized zinc propylene bis(dithiocarbamate)

COMPARATIVE EXAMPLES 1 and 2

Preparation of Wettable Powder

Ethaboxam, co-formulants and extenders were introduced into a vinyl bag and homogeneously mixed. Then, the mixture was ground to obtain the wettable powder(Table 12).

TABLE 12

| | Comparative Example | |
|---|---|---|
| | 1 | 2 |
| Ethaboxam | 12.5 | 25.0 |
| Anhydrous sodium sulfate | 15.5 | 15.5 |
| Sodium lauryl sulfate | 2 | 2 |
| Sodium lignin sulfonate | 3 | 3 |
| White carbon(Zeosil 39) | 27 | 27 |
| Kaolin | 40 | 27.5 |

(unit: weight %)

COMPARATIVE EXAMPLES 3 to 5

Preparation of Dispersible Concentrate

Ethaboxam was previously dissolved in N-methyl-2-pyrrolidone and other co-formulants and adjuvant were added thereto and dissolved to obtain the dispersible concentrate(Table 13).

TABLE 13

| | Comparative Example | | |
|---|---|---|---|
| | 3 | 4 | 5 |
| Ethaboxam | 12.5 | 8.5 | 8.5 |
| Polyoxyethylene(n = 12) cetyl ether(Koremul CE-12) | — | — | 8.5 |
| Polyoxyethylene tristyryl phenyl ether(HY-310F) | 5 | 10 | 10 |
| Polyoxyethylene(n = 20) sorbitan monolaurate(Tween 20) | 25 | — | — |
| N-methyl-2-pyrrolidone | 57.5 | 81.5 | 73.0 |

(unit: weight %)

Evaluation of Biological Activity

Enhancement of efficacy by the presence of polyoxyalkylene alkyl ether can be supported by the increase of efficacy of the fungicidal composition containing a particular polyoxyalkylene alkyl ether, as compared with that of polyoxyalkylene alkyl ether-free composition. In addition, enhancement of efficacy by combined formulation can be supported by the maintenance or the increase of efficacy of combined formulation further containing other agents for controlling plant diseases, as compared with that of single formulation having a relatively higher concentration of ethaboxam.

EXPERIMENT 1

Activity of Premixed Onepack Formulations Containing Ethaboxam and Polyoxyalkylene Alkyl Ether 1) Activity on Tomato Late Blight(*Phytophthora infestans*)

A) Preventive Activity

Tomato seeds were sown in a horticultural bed soil of pots having a diameter of 6 cm and grown under glass for 4 weeks. Spray liquids having the concentrations of 1, 5, 10, 50 and 100 mg/l as active ingredients, respectively, were preparedfrom the wettable powder and the dispersible concentrate. The spray liquids were sprayed onto tomato leaves and stems at 5 ml per pot using an atomizer and dried in a greenhouse for 24 hours. *Phytophthora infestans* was prepared at a concentration of $1 \times 10^4$ zoospores/ml and inoculated into the plants using an atomizer. In order to induce the disease, the inoculated plants were placed at 20° C. under the relative humidity of 100% for 3 to 4 days. When the incidence rate of disease in the untreated group reached 80% or more, the incidence rate of disease in each group was measured. The results are shown in the following Tables 14 and 15.

TABLE 14

Percentage of infected area (%)

| Formulation | Concentration as active ingredient (mg/l) | | | | |
|---|---|---|---|---|---|
| | 1 | 5 | 10 | 50 | 100 |
| Example 1 | 10 | 6 | 2 | 0 | 0 |
| Example 2 | 10 | 7 | 2 | 0 | 0 |
| Example 3 | 1 | 1 | 0 | 0 | 0 |
| Example 4 | 0 | 0 | 0 | 0 | 0 |
| Example 5 | 1 | 1 | 0 | 0 | 0 |
| Example 6 | 5 | 5 | 1 | 0 | 0 |
| Example 7 | 5 | 3 | 1 | 0 | 0 |
| Example 8 | 2 | 2 | 1 | 0 | 0 |
| Example 9 | 1 | 2 | 0 | 0 | 0 |
| Example 10 | 2 | 2 | 1 | 0 | 0 |
| Comparative Example 1 | 20 | 13 | 5 | 0 | 0 |
| Comparative Example 2 | 21 | 11 | 5 | 0 | 0 |
| Guardian Wettable Powder[1] | 15 | 5 | 3 | 0 | 0 |
| Untreated | | | 95 | | |

[1]Ethaboxam 25% wettable powder commercialized by Misung Ltd.

TABLE 15

Percentage of infected area (%)

| Formulation | Concentration as active ingredient (mg/l) | | | | |
|---|---|---|---|---|---|
| | 1 | 5 | 10 | 50 | 100 |
| Example 14 | 10 | 4 | 2 | 0 | 0 |
| Example 15 | 9 | 3 | 3 | 0 | 0 |
| Example 16 | 8 | 4 | 3 | 0 | 0 |
| Example 17 | 2 | 1 | 0 | 0 | 0 |
| Example 18 | 2 | 1 | 0 | 0 | 0 |
| Example 19 | 1 | 1 | 0 | 0 | 0 |
| Example 20 | 1 | 1 | 0 | 0 | 0 |
| Example 21 | 7 | 3 | 1 | 0 | 0 |
| Example 22 | 7 | 2 | 2 | 0 | 0 |
| Example 23 | 6 | 3 | 2 | 0 | 0 |

TABLE 15-continued

Percentage of infected area (%)

| Formulation | Concentration as active ingredient (mg/l) | | | | |
|---|---|---|---|---|---|
| | 1 | 5 | 10 | 50 | 100 |
| Example 24 | 4 | 3 | 2 | 0 | 0 |
| Example 25 | 2 | 2 | 0 | 0 | 0 |
| Example 26 | 1 | 2 | 1 | 0 | 0 |
| Example 27 | 1 | 1 | 0 | 0 | 0 |
| Example 28 | 1 | 1 | 0 | 0 | 0 |
| Comparative Example 3 | 12 | 6 | 3 | 0 | 0 |
| Guardian Wettable Powder[1] | 15 | 5 | 3 | 0 | 0 |
| Untreated | | | 95 | | |

[1]Ethaboxam 25% wettable powder commercialized by Misung Ltd.

As shown in the above tables, the formulations containing polyoxyalkylene alkyl ether considerably enhanced the efficacy, as compared with polyoxyalkylene alkyl ether-free formulations. Especially, the formulations containing polyoxyethylene cetyl ether had the outstanding effect, that is, superior efficacy to Guardian(Misung Ltd.) even at a half or less concentration of ethaboxam.

B) Curative Activity

Tomato seeds were sown in a horticultural bed soil of pots having a diameter of 6 cm and grown under glass for 4 weeks. *Phytophthora infestans* was prepared at a concentration of $1 \times 10^4$ zoospores/ml and inoculated into the plants using an atomizer. In order to induce the disease, the inoculated plants were placed at 20° C. under the relative humidity of 100% for 24 hours. Spray liquids having the concentrations of 1, 5, 10, 50 and 100 mg/l as active ingredient, respectively, were prepared from the wettable powder and the dispersible concentrate. The spray liquids were sprayed onto tomato leaves and stems at 5 ml per pot using an atomizer and then, the disease was induced at 20° C. under the relative humidity of 100% for 2 to 3 days. When the incidence rate of disease in the untreated group reached 80% or more, the incidence rate of disease in each group was measured. The results are shown in the following Tables 16 and 17.

TABLE 16

Percentage of infected area (%)

| Formulation | Concentration as active ingredient (mg/l) | | | | |
|---|---|---|---|---|---|
| | 1 | 5 | 10 | 50 | 100 |
| Example 1 | 17 | 9 | 5 | 0 | 0 |
| Example 2 | 19 | 11 | 7 | 0 | 0 |
| Example 3 | 4 | 2 | 1 | 0 | 0 |
| Example 4 | 3 | 2 | 0 | 0 | 0 |
| Example 5 | 3 | 1 | 0 | 0 | 0 |
| Example 6 | 9 | 7 | 3 | 0 | 0 |
| Example 7 | 10 | 6 | 2 | 0 | 0 |
| Example 8 | 4 | 3 | 1 | 0 | 0 |
| Example 9 | 5 | 2 | 2 | 0 | 0 |
| Example 10 | 5 | 2 | 1 | 0 | 0 |
| Comparative Example 1 | 40 | 17 | 13 | 1 | 0 |
| Comparative Example 2 | 37 | 15 | 12 | 1 | 0 |
| Guardian Wettable Powder[1] | 35 | 15 | 10 | 1 | 0 |
| Untreated | | | 100 | | |

[1]Ethaboxam 25% wettable powder commercialized by Misung Ltd.

TABLE 17

Percentage of infected area (%)

| Formulation | Concentration as active ingredient (mg/l) | | | | |
|---|---|---|---|---|---|
| | 1 | 5 | 10 | 50 | 100 |
| Example 14 | 15 | 8 | 5 | 0 | 0 |
| Example 15 | 12 | 7 | 5 | 0 | 0 |
| Example 16 | 10 | 7 | 7 | 0 | 0 |
| Example 17 | 2 | 1 | 1 | 0 | 0 |
| Example 18 | 3 | 1 | 1 | 0 | 0 |
| Example 19 | 1 | 0 | 0 | 0 | 0 |
| Example 20 | 3 | 1 | 0 | 0 | 0 |
| Example 21 | 7 | 6 | 3 | 0 | 0 |
| Example 22 | 8 | 3 | 3 | 0 | 0 |
| Example 23 | 7 | 3 | 2 | 0 | 0 |
| Example 24 | 7 | 4 | 3 | 0 | 0 |
| Example 25 | 3 | 1 | 0 | 0 | 0 |
| Example 26 | 2 | 1 | 1 | 0 | 0 |
| Example 27 | 2 | 0 | 0 | 0 | 0 |
| Example 28 | 1 | 1 | 1 | 0 | 0 |
| Comparative Example 3 | 20 | 11 | 8 | 1 | 0 |
| Guardian Wettable Powder[1] | 35 | 15 | 10 | 1 | 0 |
| Untreated | | | 100 | | |

[1] Ethaboxam 25% wettable powder commercialized by Misung Ltd.

As shown in the above tables, the curative activity of tomato late blight was significantly enhanced as compared with the comparative example and Guardian wettable powder where polyoxyalkylene alkyl ether was not contained. It had a similar pattern to the preventive activity thereof Accordingly, it was confirmed that the fungicidal composition of the present invention enhanced both preventive and curative activities of tomato late blight.

2) Activity on Potato Late Blight (*Phytophthora infestans*)

A) Preventive Activity

Artificial seed potatoes were sown in a horticultural bed soil of pots having a diameter of 6 cm and grown under glass for 4 weeks. Spray liquids having the concentrations of 1, 5, 10, 50 and 100 mg/l as active ingredient, respectively, were prepared from the wettable powder and the dispersible concentrate. The spray liquids were sprayed onto potato leaves and stems at 5 ml per pot using an atomizer and dried in a greenhouse for 24 hours. *Phytophthora infestans* was prepared at a concentration of $1 \times 10^4$ zoospores/ml and inoculated into the plants using an atomizer. In order to induce the disease, the inoculated plants were placed at 20° C. under the relative humidity of 100% for 3 to 4 days. When the incidence rate of disease in the untreated group reached 80% or more, the incidence rate of disease in each group was measured. The results are shown in the following Tables 18 and 19.

TABLE 18

Percentage of infected area (%)

| Formulation | Concentration as active ingredient (mg/l) | | | | |
|---|---|---|---|---|---|
| | 1 | 5 | 10 | 50 | 100 |
| Example 1 | 12 | 10 | 7 | 0 | 0 |
| Example 2 | 13 | 10 | 7 | 0 | 0 |
| Example 3 | 3 | 2 | 1 | 0 | 0 |
| Example 4 | 3 | 1 | 0 | 0 | 0 |
| Example 5 | 4 | 3 | 1 | 0 | 0 |
| Example 6 | 9 | 7 | 5 | 0 | 0 |
| Example 7 | 10 | 7 | 6 | 0 | 0 |
| Example 8 | 4 | 3 | 1 | 0 | 0 |
| Example 9 | 4 | 2 | 0 | 0 | 0 |
| Example 10 | 3 | 3 | 1 | 0 | 0 |

TABLE 18-continued

Percentage of infected area (%)

| Formulation | Concentration as active ingredient (mg/l) | | | | |
|---|---|---|---|---|---|
| | 1 | 5 | 10 | 50 | 100 |
| Comparative Example 1 | 25 | 20 | 10 | 0 | 0 |
| Comparative Example 2 | 23 | 21 | 10 | 0 | 0 |
| Guardian Wettable Powder[1] | 20 | 13 | 8 | 0 | 0 |
| Untreated | | | 100 | | |

[1] Ethaboxam 25% wettable powder commercialized by Misung Ltd.

TABLE 19

Percentage of infected area (%)

| Formulation | Concentration as active ingredient (mg/l) | | | | |
|---|---|---|---|---|---|
| | 1 | 5 | 10 | 50 | 100 |
| Example 14 | 10 | 8 | 7 | 0 | 0 |
| Example 15 | 12 | 8 | 5 | 0 | 0 |
| Example 16 | 10 | 7 | 4 | 0 | 0 |
| Example 17 | 2 | 1 | 1 | 0 | 0 |
| Example 18 | 3 | 1 | 1 | 0 | 0 |
| Example 19 | 2 | 1 | 0 | 0 | 0 |
| Example 20 | 3 | 1 | 0 | 0 | 0 |
| Example 21 | 7 | 3 | 3 | 0 | 0 |
| Example 22 | 8 | 4 | 2 | 0 | 0 |
| Example 23 | 9 | 3 | 1 | 0 | 0 |
| Example 24 | 7 | 7 | 3 | 0 | 0 |
| Example 25 | 3 | 2 | 1 | 0 | 0 |
| Example 26 | 2 | 1 | 0 | 0 | 0 |
| Example 27 | 2 | 1 | 1 | 0 | 0 |
| Example 28 | 2 | 2 | 2 | 0 | 0 |
| Comparative Example 3 | 17 | 14 | 10 | 0 | 0 |
| Guardian Wettable Powder[1] | 20 | 13 | 8 | 0 | 0 |
| Untreated | | | 100 | | |

[1] Ethaboxam 25% wettable powder commercialized by Misung Ltd.

As shown in the above tables, the preventive activity of potato late blight was similar to that of tomato late blight.

B) Curative Activity

Artificial seed potatoes were sown in a horticultural bed soil of pots having a diameter of 6 cm and grown under glass for 4 weeks. *Phytophtrlora infestans* was prepared at a concentration of $1 \times 10^4$ zoospores/ml and inoculated into the plants using an atomizer. In order to induce the disease, the inoculated plants were placed at 20° C. under the relative humidity of 100% for 24 hours. Spray liquids having the concentrations of 1, 5, 10, 50 and 100 mg/l as active ingredient, respectively, were prepared from the wettable powder and the dispersible concentrate. The spray liquids were sprayed onto potato leaves and stems at 5 ml per pot using an atomizer and then, the disease was induced at 20° C. under the relative humidity of 100% for 2 to 3 days. When the incidence rate of disease in the untreated g,euip reached 80% or more, the incidence rate of disease in each group was measured. The results are shown in the following Tables 20 and 21.

TABLE 20

Percentage of infected area (%)

| Formulation | Concentration as active ingredient (mg/l) | | | | |
|---|---|---|---|---|---|
| | 1 | 5 | 10 | 50 | 100 |
| Example 1 | 16 | 11 | 6 | 0 | 0 |
| Example 2 | 16 | 13 | 7 | 0 | 0 |

TABLE 20-continued

Percentage of infected area (%)

| | Concentration as active ingredient (mg/l) | | | | |
|---|---|---|---|---|---|
| Formulation | 1 | 5 | 10 | 50 | 100 |
| Example 3 | 5 | 2 | 1 | 0 | 0 |
| Example 4 | 3 | 2 | 1 | 0 | 0 |
| Example 5 | 3 | 3 | 1 | 0 | 0 |
| Example 6 | 10 | 7 | 4 | 0 | 0 |
| Example 7 | 14 | 9 | 2 | 0 | 0 |
| Example 8 | 4 | 3 | 2 | 0 | 0 |
| Example 9 | 3 | 3 | 2 | 0 | 0 |
| Example 10 | 5 | 3 | 1 | 0 | 0 |
| Comparative Example 1 | 38 | 17 | 13 | 1 | 0 |
| Comparative Example 2 | 35 | 16 | 13 | 1 | 0 |
| Guardian Wettable Powder[1] | 40 | 17 | 15 | 3 | 0 |
| Untreated | | | 100 | | |

1) Ethaboxam 25% wettable powder commercialized by Misung Ltd.

TABLE 21

Percentage of infected area (%)

| | Concentration as active ingredient (mg/l) | | | | |
|---|---|---|---|---|---|
| Formulation | 1 | 5 | 10 | 50 | 100 |
| Example 14 | 17 | 13 | 7 | 0 | 0 |
| Example 15 | 15 | 12 | 5 | 0 | 0 |
| Example 16 | 13 | 12 | 5 | 0 | 0 |
| Example 17 | 4 | 3 | 0 | 0 | 0 |
| Example 13 | 5 | 2 | 1 | 0 | 0 |
| Example 19 | 3 | 1 | 0 | 0 | 0 |
| Example 20 | 5 | 2 | 1 | 0 | 0 |
| Example 21 | 11 | 8 | 5 | 0 | 0 |
| Example 22 | 10 | 7 | 4 | 0 | 0 |
| Example 23 | 9 | 7 | 5 | 0 | 0 |
| Example 24 | 13 | 8 | 5 | 0 | 0 |
| Example 25 | 5 | 4 | 2 | 0 | 0 |
| Example 26 | 5 | 3 | 2 | 0 | 0 |
| Example 27 | 4 | 3 | 1 | 0 | 0 |
| Example 28 | 6 | 2 | 1 | 0 | 0 |
| Comparative Example 3 | 30 | 12 | 10 | 1 | 0 |
| Guardian Wettable Powder[1] | 40 | 17 | 15 | 3 | 0 |
| Untreated | | | 100 | | |

[1] Ethaboxam 25% wettable powder commercialized by Misung Ltd.

As shown in the above tables, the curative activity of potato late blight was also similar to that of tomato late blight. Accordingly, it was confirmed that the fungicidal composition of the present invention enhanced both preventive and curative activities of potato late blight.

3) Activity on Cucumber Downy Mildew (*Pseudoperonospora cubensis*)

A) Preventive Activity

Cucumber seeds were sown in a horticultural bed soil of pots having a diameter of 6 cm and grown under glass for 4 weeks. Spray liquids having the concentrations of 1, 5, 10, 50 and 100 mg/l as active ingredient, respectively, were prepared from the wettable powder and the dispersible concentrate. The spray liquids were sprayed onto cucumber leaves and stems at 5 ml per pot using an atomizer and dried in a greenhouse for 24 hours. *Pseudoperonospora cubensis* was prepared at a concentration of $5 \times 10^4$ zoosporangia/ml and inoculated into the plants using an atomizer. In order to induce the disease, the inoculated plants were placed at 20° C. under the relative humidity of 100% for 3 to 4 days. When the incidence rate of disease in the untreated group reached 80% or more, the incidence rate of disease in each group was measured. The results are shown in the following Tables 22 and 23.

TABLE 22

Percentage of infected area (%)

| | Concentration as active ingredient (mg/l) | | | | |
|---|---|---|---|---|---|
| Formulation | 1 | 5 | 10 | 50 | 100 |
| Example 1 | 7 | 4 | 4 | 0 | 0 |
| Example 2 | 6 | 6 | 3 | 0 | 0 |
| Example 3 | 2 | 1 | 0 | 0 | 0 |
| Example 4 | 1 | 1 | 0 | 0 | 0 |
| Example 5 | 1 | 1 | 0 | 0 | 0 |
| Example 6 | 5 | 5 | 2 | 0 | 0 |
| Example 7 | 4 | 3 | 2 | 0 | 0 |
| Example 8 | 2 | 2 | 1 | 0 | 0 |
| Example 9 | 1 | 1 | 0 | 0 | 0 |
| Example 10 | 2 | 1 | 1 | 0 | 0 |
| Comparative Example 1 | 16 | 10 | 7 | 0 | 0 |
| Comparative Example 2 | 15 | 10 | 7 | 0 | 0 |
| Guardian Wettable Powder[1] | 13 | 8 | 6 | 0 | 0 |
| Untreated | | | 80 | | |

[1] Ethaboxam 25% wettable powder commercialized by Misung Ltd.

TABLE 23

Percentage of infected area (%)

| | Concentration as active ingredient (mg/l) | | | | |
|---|---|---|---|---|---|
| Formulation | 1 | 5 | 10 | 50 | 100 |
| Example 14 | 8 | 8 | 6 | 0 | 0 |
| Example 15 | 10 | 7 | 6 | 0 | 0 |
| Example 16 | 9 | 6 | 5 | 0 | 0 |
| Example 17 | 3 | 2 | 0 | 0 | 0 |
| Example 18 | 2 | 2 | 0 | 0 | 0 |
| Example 19 | 2 | 1 | 0 | 0 | 0 |
| Example 20 | 2 | 2 | 0 | 0 | 0 |
| Example 21 | 8 | 7 | 4 | 0 | 0 |
| Example 22 | 7 | 5 | 3 | 0 | 0 |
| Example 23 | 7 | 5 | 1 | 0 | 0 |
| Example 24 | 9 | 6 | 3 | 0 | 0 |
| Example 25 | 4 | 3 | 1 | 0 | 0 |
| Example 26 | 2 | 2 | 1 | 0 | 0 |
| Example 27 | 2 | 2 | 2 | 0 | 0 |
| Example 28 | 3 | 3 | 0 | 0 | 0 |
| Comparative Example 3 | 14 | 10 | 8 | 0 | 0 |
| Guardian Wettable Powder[1] | 13 | 6 | 6 | 0 | 0 |
| Untreated | | | 80 | | |

[1] Ethaboxam 25% wettable powder commercialized by Misung Ltd.

As shown in the above tables, in the untreated group, the incidence rate of cucumber downy mildew was slightly lower than tomato and potato late blights because of its characteristics, but the preventive activity of cucumber downy mildew was similar to that of tomato and potato late blights.

B) Curative Activity

Cucumber seeds were sown in a horticultural bed soil of pots having a diameter of 6 cm and grown under glass for 4 weeks. *Pseudoperonospora cubensis* was prepared at a concentration of $5 \times 10^4$ zoosporangia/ml and inoculated into the plants using an atomizer. In order to induce the disease, the inoculated plants were placed at 20° C. under the relative humidity of 100% for 24 hours. Spray liquids having the concentrations of 1, 5, 10, 50 and 100 mg/l as active ingredient, respectively, were prepared from the wettable powder and the dispersible concentrate. The spray liquids were sprayed onto cucumber leaves and stems at 5 ml per pot using an atomizer and then, the disease was induced at 20° C. under the relative humidity of 100% for 2 to 3 days. When the incidence rate of disease in the untreated group reached 80% or more, the incidence rate of disease in each group was measured. The results are shown in the following Tables 24 and 25.

TABLE 24

Percentage of infected area (%)

| Formulation | Concentration as active ingredient (mg/l) | | | | |
|---|---|---|---|---|---|
| | 1 | 5 | 10 | 50 | 100 |
| Example 1 | 13 | 10 | 5 | 0 | 0 |
| Example 2 | 12 | 8 | 5 | 0 | 0 |
| Example 3 | 5 | 2 | 1 | 0 | 0 |
| Example 4 | 2 | 1 | 1 | 0 | 0 |
| Example 5 | 4 | 2 | 0 | 0 | 0 |
| Example 6 | 8 | 7 | 5 | 0 | 0 |
| Example 7 | 10 | 7 | 6 | 0 | 0 |
| Example 8 | 4 | 2 | 0 | 0 | 0 |
| Example 9 | 5 | 2 | 0 | 0 | 0 |
| Example 10 | 4 | 1 | 1 | 0 | 0 |
| Comparative Example 1 | 30 | 14 | 11 | 2 | 0 |
| Comparative Example 2 | 31 | 16 | 11 | 1 | 0 |
| Guardian Wettable Powder[1] | 30 | 25 | 10 | 2 | 0 |
| Untreated | | | 80 | | |

[1]Ethaboxam 25% wettable powder commercialized by Misung Ltd.

TABLE 25

Percentage of infected area (%)

| Formulation | Concentration as active ingredient (mg/l) | | | | |
|---|---|---|---|---|---|
| | 1 | 5 | 10 | 50 | 100 |
| Example 14 | 16 | 13 | 6 | 0 | 0 |
| Example 15 | 13 | 10 | 8 | 0 | 0 |
| Example 16 | 11 | 11 | 5 | 0 | 0 |
| Example 17 | 5 | 3 | 1 | 0 | 0 |
| Example 18 | 3 | 3 | 1 | 0 | 0 |
| Example 19 | 4 | 2 | 1 | 0 | 0 |
| Example 20 | 4 | 3 | 0 | 0 | 0 |
| Example 21 | 9 | 7 | 4 | 0 | 0 |
| Example 22 | 8 | 8 | 4 | 0 | 0 |
| Example 23 | 8 | 6 | 5 | 0 | 0 |
| Example 24 | 9 | 7 | 5 | 0 | 0 |
| Example 25 | 6 | 3 | 4 | 0 | 0 |
| Example 26 | 3 | 2 | 0 | 0 | 0 |
| Example 27 | 4 | 2 | 0 | 0 | 0 |
| Example 28 | 5 | 2 | 1 | 0 | 0 |
| Comparative Example 3 | 21 | 12 | 7 | 1 | 0 |
| Guardian Wettable Powder[1] | 30 | 15 | 10 | 2 | 0 |
| Untreated | | | 100 | | |

[1]Ethaboxam 25% wettable powder commercialized by Misung Ltd.

As shown in the above tables, the curative activity of cucumber downy mildew was also similar to that of tomato and potato late blights. Accordingly, it was confirmed that the fungicidal composition of the present invention enhanced both preventive and curing activities of cucumber downy mildew.

EXPERIMENT 2

Activity of Tank-mixed Formulations Containing Polyoxyalkylene Alkyl Ether

1) Activity on Tomato Late Blight(*Phytophthora infestans*)

A) Preventive Activity

Tomato seeds were sown in a horticultural bed soil of pots having a diameter of 6 cm and grown under glass for 4 weeks. Spray liquids having the concentrations of 1, 5, 10, 50 and 100 mg/l as active ingredient, respectively, and containing 320 mg/l of polyoxyalkylene alkyl ethers were prepared from the wettable powder of Comparative Example 1 and polyoxyalkylene alkyl ethers of the following Table 26. The spray liquids were sprayed onto tomato leaves and stems at 5 ml per pot using an atomizer and dried in a greenhouse for 24 hours. *Phytophthora infestans* was prepared at a concentration of $1 \times 10^4$ zoospores/ml and inoculated into the plants using an atomizer. In order to induce the disease, the inoculated plants were placed at 20° C. under the relative humidity of 100% for 3 to 4 days. When the incidence rate of disease in the untreated group reached 80% or more, the incidence rate of disease in each group was measured. The results are shown in the following Table 26.

TABLE 26

Percentage of infected area (%)

| Polyoxyethylene alkyl ether(320 mg/l) in a spray liquid | Concentration as active ingredient (mg/l) | | | | |
|---|---|---|---|---|---|
| | 1 | 5 | 10 | 50 | 100 |
| Polyoxyethylene(n = 7) lauryl ether(KONION LA-7) | 12 | 8 | 3 | 0 | 0 |
| Polyoxyethylene(n = 10) lauryl ether(KONION LA-10) | 12 | 6 | 2 | 0 | 0 |
| Polyoxyethylene(n = 20) lauryl ether(KONION LA-20) | 9 | 7 | 2 | 1 | 0 |
| Polyoxyethylene(n = 7) cetyl ether(Koremul CE-7) | 5 | 2 | 2 | 0 | 0 |
| Polyoxyethylene(n = 10) cetyl ether(Brij 56) | 2 | 2 | 1 | 0 | 0 |
| Polyoxyethylene(n = 12) cetyl ether(Koremul CE-12) | 2 | 0 | 0 | 0 | 0 |
| Polyoxyethylene(n = 20) cetyl ether(Brij 58) | 1 | 1 | 0 | 0 | 0 |
| Polyoxyethylene(n = 7) oleyl ether(Koremul OE-7) | 6 | 3 | 2 | 0 | 0 |
| Polyoxyethylene(n = 10) oleyl ether(Koremul OE-10) | 6 | 5 | 1 | 0 | 0 |
| Polyoxyethylene(n = 15) oleyl ether(KONION OA-15) | 3 | 3 | 0 | 0 | 0 |
| Polyoxyethylene(n = 20) oleyl ether(Koremul OE-20) | 4 | 1 | 0 | 0 | 0 |
| Polyoxyethylene(n = 7) stearyl ether(Koremul SE-7) | 7 | 6 | 1 | 1 | 0 |
| Polyoxyethylene(n = 10) stearyl ether(Brij 76) | 2 | 1 | 1 | 0 | 0 |
| Polyoxyethylene(n = 14) stearyl ether(Koremul SE-14) | 1 | 0 | 0 | 0 | 0 |
| Polyoxyethylene(n = 20) stearyl ether(Brij 78) | 2 | 1 | 0 | 0 | 0 |
| Polyoxyethylene alkyl ether-free | 22 | 14 | 5 | 0 | 0 |

As shown in the above table, the tank-mixed formulation containing polyoxyalkylene alkyl ether was confirmed to enhance the preventive activity of tomato late blight in the same manner as the premixed one-pack formulation.

B) Curative Activity

Tomato seeds were sown in a horticultural bed soil of pots having a diameter of 6 cm and grown under glass for 4 weeks. *Phytophthora infestans* was prepared at a concentration of $1 \times 10^4$ zoospores/ml and inoculated into the plants using an atomizer. In order to induce the disease, the inoculated plants were placed at 20° C. under the relative humidity of 100% for 24 hours. Spray liquids having the concentrations of 1, 5, 10, 50 and 100 mg/l as active ingredient, respectively, and containing 320 mgll of polyoxyalkylene alkyl ethers were prepared from the wettable powder of Comparative Example 1 and polyoxyalkylene alkyl ethers of the following Table 27. The spray liquids were sprayed onto tomato leaves and stems at 5 ml per pot using an atomizer and then, the disease was induced at 20° C. under the relative humidity of 100% for 2 to 3 days. When the incidence rate of disease in the untreated group reached 80% or more, the incidence rate of disease in each group was measured. The results are shown in the following Table 27.

TABLE 27

Percentage of infected area (%)

| Polyoxyethylene alkyl ether(320 mg/l) in a spray liquid | Concentration as active ingredient (mg/l) | | | | |
|---|---|---|---|---|---|
| | 1 | 5 | 10 | 50 | 100 |
| Polyoxyethylene(n = 7) lauryl ether(KONION LA-7) | 16 | 12 | 5 | 0 | 0 |
| Polyoxyethylene(n = 10) lauryl ether(KONION LA-10) | 15 | 6 | 3 | 0 | 0 |
| Polyoxyethylene(n = 20) lauryl ether(KONION LA-20) | 13 | 5 | 3 | 1 | 0 |
| Polyoxyethylene(n = 7) cetyl ether(Koremul CE-7) | 5 | 4 | 1 | 0 | 0 |
| Polyoxyethylene(n = 10) cetyl ether(Brij 56) | 3 | 2 | 0 | 0 | 0 |
| Polyoxyethylene(n = 12) cetyl ether(Koremul CE-12) | 2 | 1 | 0 | 0 | 0 |
| Polyoxyethylene(n = 20) cetyl ether(Brij 58) | 2 | 1 | 1 | 0 | 0 |
| Polyoxyethylene(n = 7) oleyl ether(Koremul OE-7) | 9 | 8 | 4 | 0 | 0 |
| Polyoxyethylene(n = 10) oleyl ether(Koremul OE-10) | 6 | 7 | 4 | 0 | 0 |
| Polyoxyethylene(n = 15) oleyl ether(KONION OE-15) | 5 | 3 | 2 | 0 | 0 |
| Polyoxyethylene(n = 20) oleyl ether(Koremul OE-20) | 5 | 4 | 1 | 0 | 0 |
| Polyoxyethylene(n = 7) stearyl ether(Koremul SE-7) | 6 | 5 | 3 | 1 | 0 |
| Polyoxyethylene(n = 10) stearyl ether(Brij 76) | 2 | 1 | 0 | 0 | 0 |
| Polyoxyethylene(n = 14) stearyl ether(Koremul SE-14) | 3 | 1 | 0 | 0 | 0 |
| Polyoxyethylene(n = 20) stearyl ether(Brij 78) | 2 | 1 | 1 | 0 | 0 |
| Polyoxyethylene alkyl ether-free | 43 | 20 | 13 | 3 | 0 |

As shown in the above table, the tank-mixed formulation containing polyoxyalkylene alkyl ether was confirmed to enhance the curative activity of tomato late blight in the same manner as the premixed one-pack formulation. Accordingly, it was confirmed that the fungicidal composition of the present invention enhanced efficacy not only in the premixed one-pack formulation but also in the tank-mixed formulation.

EXPERIMENT 3

Activity of the Fungicidal Composition Containing Additional Agents for Controlling Plant Diseases Other Than Ethaboxam 1) Residual Activity on Tomato Late Blight(*Plytophthora infestans*)

Tomato seeds were sown in a horticultural bed soil of pots having a diameter of 6 cm and grown under glass for 4 weeks. Spray liquids having the concentrations of 100 and 200 mg/l as the product, respectively, were prepared from the wettable powder. The spray liquids were sprayed onto tomato leaves and stems at 5 ml per pot using an atomizer and dried in a greenhouse for 24 hours. *Phytophthora infestans* was prepared at a concentration of $1\times10^4$ zoospores/ml and inoculated into the plants using an atomizer at 1, 5 and 10 days after spraying the liquids, respectively. In order to induce the disease, the inoculated plants were placed at 20° C. under the relative humidity of 100°C. The incidence rate of disease was measured at 3 to 4 days after the final inoculation. The results are shown in the following Table 28.

TABLE 28

Percentage of infected area (%)

| Formulation | Concentration of spray (mg/l; as the product) | Inoculation day after spraying the liquid | | |
|---|---|---|---|---|
| | | 1 day | 5 days | 10 days |
| Example 32 | 100 | 8 | 10 | 26 |
| Example 33 | | 7 | 18 | 24 |
| Example 34 | | 8 | 13 | 28 |
| Example 35 | | 8 | 13 | 31 |
| Example 36 | | 5 | 10 | 13 |
| Example 37 | | 10 | 10 | 18 |
| Example 38 | | 5 | 13 | 16 |
| Example 39 | | 6 | 10 | 23 |
| Example 40 | 200 | 5 | 8 | 46 |
| Example 41 | | 13 | 15 | 28 |
| Example 42 | | 6 | 11 | 19 |
| Example 43 | | 1 | 4 | 13 |
| Example 44 | | 7 | 7 | 20 |
| Example 4 | 100 | 10 | 9 | 24 |
| Guardian | | 7 | 15 | 34 |
| Untreated | — | 100 | | |

As shown in the above table, the combined formulations containing ethaboxam and additional agents effective for crop downy mildew or rot exhibited outstanding or similar efficacy even at a lower quantity of ethaboxam, as compared with the formulation of Example 4 and Guardian wettable powder. Especially, the residual activity was remarkably enhanced in the combined formulation of ethaboxam and mancozeb having the effect of preventing various plant diseases. Accordingly, it was confirmed that combined formulations containing ethaboxam and other agents for controlling plant diseases had the enhanced the efficacy. In particular, the quantity of ethaboxam which needs to be applied could be remarkably reduced by combining preventive agents with ethaboxam.

EXPERIMENT 4

Relationship of the Concentration of Polyoxyallylene Alkyl Ether and Foliar Penetration of Ethaboxam In order to investigate the relationship of the concentration of polyoxyalkylene alkyl ether and the foliar penetration of ethaboxam, foliar penetration experiment was carried out using radioisotope [$C^{14}$]-labeled ethaboxam as follows.

Cucumber seeds were sown in a horticultural bed soil of pots having a diameter of 6 cm and grown under glass for 3 weeks. 10 mg of the formulation prepared in the comparative example was diluted in 10 ml of tap water. 20 $\mu$l of the diluted solution was taken and thereto was added 1.0 $\mu$Ci of ethaboxam labeled with $C^{14}$(81.7 $\mu$Ci/mg) to prepare the diluted ethaboxam formulation labeled with $C^{14}$. The diluted solution was spotted on the foliage of cucumber at a precise amount of 10 $\mu$l using a microsyringe. After spotting, the cucumbers were placed in a greenhouse for 24 hours.

The plants were cut at a distance of 1 cm from the bottom of soil and the cuts were introduced into 250 ml Erlenmeyer flaska 50 ml of the mixed solution of acetonitrile and distilled water(volume ratio=1:4) was added thereto and then, the flask was plugged and shaken for 1 minute. Radioactivity of $C^{14}$-ethaboxam in the solution was measured with a liquid scintillation counter and the residue was combusted with a sample oxidizer to collect $C^{14}$-carbon dioxide, which was analyzed with the liquid scintillation counter.

Foliar penetration of ethaboxam is calculated by subtracting radioactivity in the solution from the total radioactivity, which is identical with radioactivity in the residue. The results are shown in the following Table 29.

TABLE 29

| Formulation | Degree of penetration (%) |
|---|---|
| Comparative Example 1 | 0 |
| Example 11 | 0 |
| Example 12 | 3 |
| Example 13 | 9 |
| Comparative Example 4 | 0 |
| Comparative Example 5 | 8 |
| Example 29 | 15 |
| Example 30 | 24 |
| Example 31 | 40 |

As can be seen from the above, ethaboxam was hardly penetrated into plants in the absence of adjuvant and the penetration was increased in proportion to the content of adjuvant. In addition, it was confirmed that dispersible concentrate had a higher permeability than wettable powder. This suggests that enhancement of efficacy is co-related with the increase of penetration in the presence of polyoxyalkylene alkyl ether. However, enhancement of efficacy is co-related with, but may not be proportional to, increase of penetration. That is, the efficacy may be changed depending on environments within or outside of plants, physiological factors of plants or characteristics of pathogens.

INDUSTRIAL APPLICABILITY

The fungicidal composition in accordance with the present invention not only enhances efficacy of ethaboxam but also reduces its quantity which needs to be applied thereby to reduce production costs of active ingredients and to minimize their quantity applied to the environment and thus, contributes to the preservation of agricultural ecosystem.

What is claimed is:
1. A fungicidal composition which comprises N-(α-cyano-2-thenyl)-4-ethyl-2-(ethylamino)-5-thiazolecarboxamide (ethaboxam) of the formula (I):

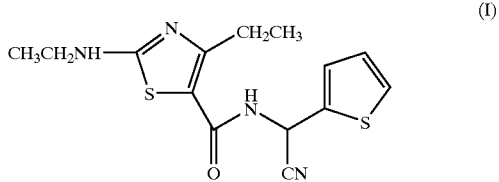

and polyoxyalkylene alkyl ether wherein the weight ratio of ethaboxam to polyoxyalkylene alkyl ether is from about 1:0.5 to about 1:10.

2. The composition according to claim 1, wherein said polyoxyalkylene alkyl ether is selected from the group consisting of polyoxyethylene lauryl ether, polyoxyethylene cetyl ether, polyoxyethylene stearyl ether and polyoxyethylene oleyl ether, each of which has an average of 7 to 20 ethylene oxide units per molecule.

3. The composition according to claim 1 which further comprises one or more carriers or surfactants.

4. The composition according to claim 1 which further comprises one or more of the compounds selected from the group consisting of carriers, surfactants, co-formulants, extenders, solvents, dispersing agents, wetting agents, diluents, and adjuvants for preventing or curing plant diseases.

5. A method for controlling undesired phytopathogens, which have attacked plants which comprises applying to plants a formulation prepared from the composition according to any one of claims 1 to 4 wherein said formulation comprises about 30 to about 300 mg/l of ethaboxam and about 100 to 2000 mg/l of polyoxyethylene alkyl ether.

6. The composition according to claim 1 which further comprises one or more of the compounds selected from the group consisting of carriers, surctants, co-formulants, extenders, solvents, dispersing agents, wetting agents, diluents, and adjuvants for curing plant diseases.

7. A method for enhancing the fungicidal activity of ethaboxam which comprises adding polyoxyalkylene alkyl ether selected from the group consisting of polyoxyethylene lauryl ether, polyoxyethylene cetyl ether, polyoxyethylene stearyl ether and polyoxyethylene oleyl ether, each of which has an average of 7 to 20 ethylene oxide units per molecule, to ethaboxam.

* * * * *